United States Patent
Albert et al.

(10) Patent No.: US 11,413,152 B2
(45) Date of Patent: Aug. 16, 2022

(54) MODULAR ACETABULAR TRIAL LINER SYSTEM

(71) Applicant: DePuy Ireland Unlimited Company, Ringaskiddy (IE)

(72) Inventors: Dustin N. Albert, Warsaw, IN (US); Conner D. Lett, Richmond, IN (US)

(73) Assignee: DePuy Ireland Unlimited Company, Ringaskiddy (IE)

( * ) Notice: Subject to any disclaimer, the term of this patent is extended or adjusted under 35 U.S.C. 154(b) by 79 days.

(21) Appl. No.: 16/695,940

(22) Filed: Nov. 26, 2019

(65) Prior Publication Data

US 2021/0154016 A1    May 27, 2021

(51) Int. Cl.
*A61F 2/34* (2006.01)
*A61F 2/46* (2006.01)
*A61F 2/30* (2006.01)

(52) U.S. Cl.
CPC .............. *A61F 2/34* (2013.01); *A61F 2/4609* (2013.01); *A61F 2/4684* (2013.01); *A61F 2002/30604* (2013.01); *A61F 2002/3401* (2013.01); *A61F 2220/0041* (2013.01); *A61F 2310/00011* (2013.01)

(58) Field of Classification Search
CPC ................ A61F 2/34; A61F 2002/3403; A61F 2002/3406; A61F 2002/3412; A61F 2002/3448; A61F 2002/3432; A61F 2002/3445
See application file for complete search history.

(56) References Cited

U.S. PATENT DOCUMENTS

| | | | | |
|---|---|---|---|---|
| 4,955,919 A | * | 9/1990 | Pappas | A61F 2/3603 623/22.26 |
| 5,658,338 A | * | 8/1997 | Tullos | A61B 17/7098 623/22.39 |
| 5,879,401 A | * | 3/1999 | Besemer | A61F 2/4684 623/22.28 |
| 2002/0107577 A1 | * | 8/2002 | Storer | A61F 2/34 623/22.28 |
| 2005/0060040 A1 | * | 3/2005 | Auxepaules | A61F 2/4609 623/22.18 |
| 2007/0106392 A1 | * | 5/2007 | Servidio | A61F 2/4637 623/22.28 |
| 2012/0185059 A1 | * | 7/2012 | Vankoski | A61F 2/4684 623/22.24 |
| 2013/0204388 A1 | * | 8/2013 | Meridew | A61F 2/34 623/22.36 |
| 2013/0325139 A1 | | 12/2013 | Steiner et al. | |

* cited by examiner

*Primary Examiner* — Anu Ramana
(74) *Attorney, Agent, or Firm* — Barnes & Thornburg LLP

(57) ABSTRACT

A trial liner for use in a hip arthroplasty surgical procedure is disclosed. The trial liner includes a rim and a semi-hemispherical body attached to the rim. The semi-hemispherical body includes a concave inner wall extending inwardly from the rim to define a cavity, a convex outer wall extending from the rim opposite the inner wall, and an interior wall extending between the inner wall and the outer wall and defining an opening at an apex of the semi-hemispherical body. The semi-hemispherical body is adapted to deflect and modify the opening, when pressed against a head of a screw, to accept the head of the screw within the opening. A system that includes the trial liner and the screw, and a method for using the system in a surgical procedure, are also disclosed.

16 Claims, 15 Drawing Sheets

MODULAR ACETABULAR TRIAL LINER SYSTEM

TECHNICAL FIELD

The present disclosure relates generally to orthopaedic prosthetic components and, more particularly, to acetabular prosthetic components.

BACKGROUND

Joint arthroplasty is a surgical procedure in which a patient's natural joint is replaced by a prosthetic joint. In a hip arthroplasty procedure, at least a portion of a patient's hip ball and socket joint is replaced with one or more corresponding prosthetic components. For example, the socket portion of the joint, known as the acetabulum, may be replaced with an acetabular prosthetic component and/or the ball portion of the joint, known as the femoral head, may be replaced with a femoral head prosthetic component. Typically, during a hip arthroplasty procedure, a surgeon may iteratively test the secureness of fit and range of motion provided by different trial components of the prosthetic joint. Testing the fit and range of motion provided by different trial components involves temporarily securing each component in the patient, testing the fit and range of motion provided by the components, removing one or more of the components, and replacing one or more of the component with other trial component(s). The iterative process of testing different trial components consumes time and, as hip arthroplasty procedures are becoming more commoditized, surgical efficiency is of utmost importance.

SUMMARY

In one aspect, the present disclosure includes a trial liner for use in a hip arthroplasty surgical procedure. The trial liner includes a rim and a semi-hemispherical body attached to the rim. The semi-hemispherical body includes a concave inner wall extending inwardly from the rim to define a cavity, a convex outer wall extending from the rim opposite the inner wall, and an interior wall extending between the inner wall and the outer wall and defining an opening at an apex of the semi-hemispherical body. The semi-hemispherical body is adapted to deflect and modify the opening, when pressed against a head of a screw, to accept the head of the screw within the opening.

In another aspect, the present disclosure includes a modular acetabular trial liner system. The modular acetabular trial liner system includes a screw that has a head and a threaded proximal portion. The modular acetabular trial liner system also includes a trial liner having a rim and a semi-hemispherical body attached to the rim. The semi-hemispherical body includes (i) a concave inner wall extending inwardly from the rim to define a cavity, (ii) a convex outer wall extending from the rim opposite the inner wall, and (iii) an interior wall extending between the inner wall and the outer wall and defining an opening at an apex of the semi-hemispherical body. The semi-hemispherical body is adapted to deflect and modify the opening, when pressed against the head of the screw, to accept the head of the screw within the opening.

In yet another aspect, the present disclosure includes a method for using a modular acetabular trial liner system in a hip arthroplasty surgical procedure that includes pressing a trial liner shaped to be received into a trial shell for an acetabulum onto a distal portion of a screw to cause a body of the trial liner to deflect to accept the distal portion of the screw into an opening of the trial liner. The method also includes rotating the screw to secure the trial liner and the screw to the trial shell.

BRIEF DESCRIPTION OF THE DRAWINGS

The concepts described herein are illustrated by way of example and not by way of limitation in the accompanying figures. For simplicity and clarity of illustration, elements illustrated in the figures are not necessarily drawn to scale. Where considered appropriate, reference labels have been repeated among the figures to indicate corresponding or analogous elements. The detailed description particularly refers to the accompanying figures in which.

DETAILED DESCRIPTION OF THE DRAWINGS

Figure 1:
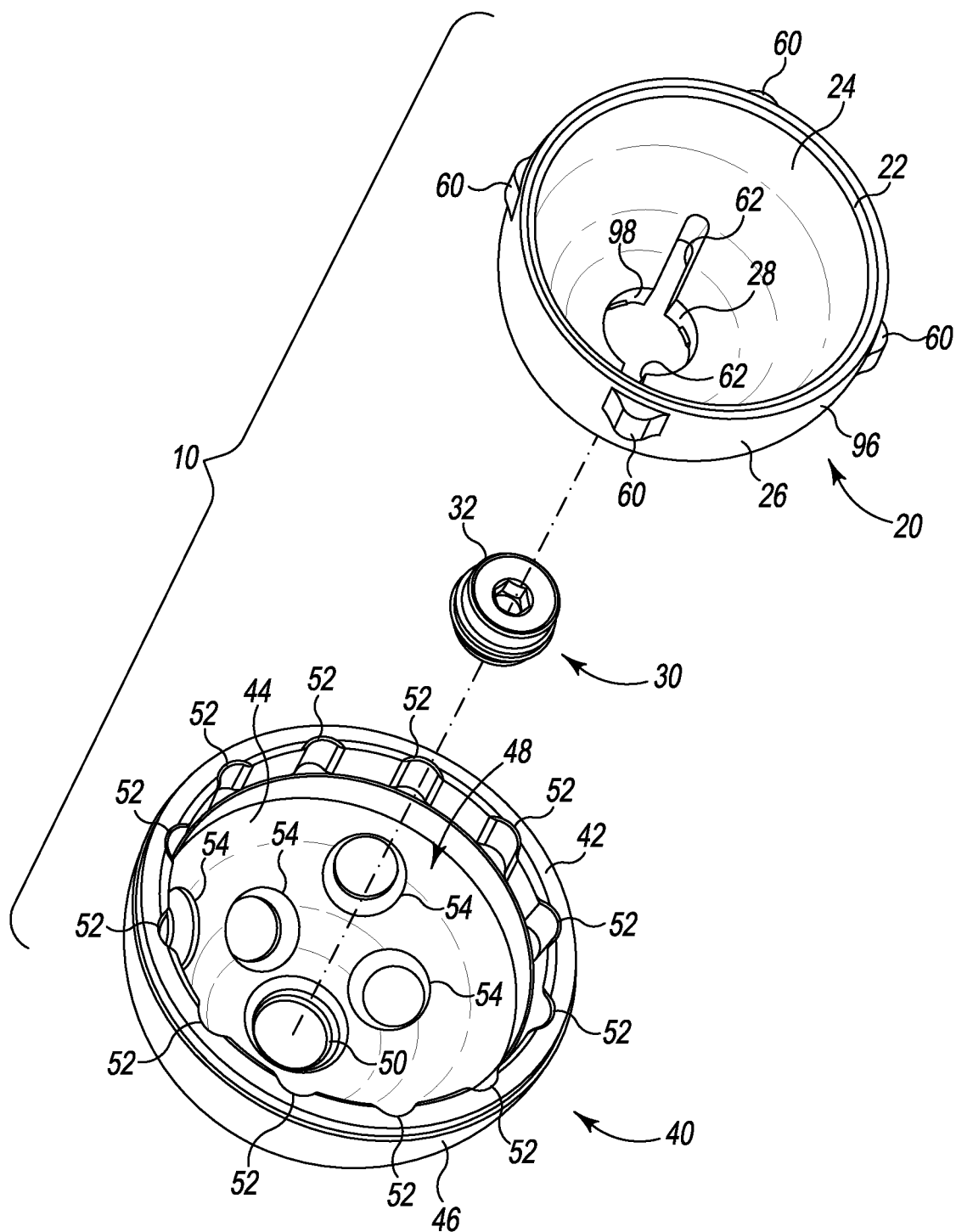
FIG. 1 is an exploded perspective view of an embodiment of a modular acetabular trial liner system.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

Terms representing anatomical references, such as anterior, posterior, medial, lateral, superior, inferior, etcetera, may be used throughout the specification in reference to the orthopaedic implants or prostheses and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring now to FIG. 1, a modular acetabular trial liner system 10 includes multiple separate components, which may be coupled together as discussed in more detail below. Illustratively, the modular acetabular trial liner system includes a trial liner 20, a threaded screw 30, and an acetabular shell 40. The shell 40 is shaped to fit within a surgically prepared acetabulum of a patient during a hip arthroplasty surgical procedure. The shell 40, in the illustrative embodiment, includes a rim 42 and a concave inner wall 44 that extends inwardly from the rim 42 to define a cavity 48 into which the screw 30 and trial liner 20 are received. The shell 40 also includes a convex outer wall 46 that extends from the rim 42 and is shaped to engage with the patient's acetabulum. In some embodiments, the inner wall 44 and outer wall 46 may be shaped to define one or more threaded bores 54 through which additional screws (not shown) may be threaded to secure the shell 40 in the patient's acetabulum. In the illustrative embodiment, the inner wall 44 is shaped to define, at a polar apex, a threaded recess 50 that receives the screw 30.

Unlike some known trial liner systems, the screw 30 and trial liner 20 are modular, in that they are not permanently fused together. Rather, the trial liner 20 includes a rim 22 and a semi-hemispherical body 96 attached to the rim 22. The semi-hemispherical body 96 includes an inner wall 24 and an outer wall 26 that extend from the rim 22, and an interior wall 98 that extends between the inner wall 24 and outer wall 26. The inner wall 24 defines an opening 28 (e.g., a cylindrical opening) at an apex of the body 96 that is adapted to fit over a distal portion 32 (e.g., head) of the screw 30 and secure the trial liner 20 to the screw 30. The semi-hemispherical body 96 has a generally hemispherical shape with the inner wall 24 being concave and the outer wall 26 being convex, although the semi-hemispherical body 96 may not define a perfect hemisphere. Further, in the illustrative embodiment, the body 96 of the trial liner 20 is made from a material (e.g., a polymeric material such as polyurethane) that is softer than the material (e.g., metal) of the screw 30. As such, in the illustrative embodiment, the body 96 will deflect (e.g., bend) as the trial liner 20 is pressed onto the distal portion 32 (e.g., head) of the screw 30 (e.g., by the surgeon or a surgeon's assistant), to allow the distal portion 32 to securely fit within the opening 28. Similarly, with sufficient force, the trial liner 20 may be separated from the screw 30, without displacing or causing damage to any other components of the system 10.

While one trial liner 20 is shown in FIG. 1, the system 10 may include multiple trial liners 20 having the features described above, while also having different thicknesses and/or geometries (e.g., having one or more augments) to change the fit of a femoral head (e.g., a prosthetic femoral head) within the trial liner (e.g., within a cavity defined by the inner wall 24) and change the range of motion provided by the system 10. As such, during a hip arthroplasty surgical procedure, the surgeon may rapidly test the fit and range of motion provided by each of multiple trial liners 20 (e.g., by pressing each trial liner 20 onto the screw 30, testing, and then pulling the trial liner 20 off of the screw 30), without having to screw and unscrew each trial liner into and out of the shell 40.

In the illustrative embodiment of FIG. 1, to contribute to the ability of the body 96 of the trial liner 20 to deflect (e.g., to accommodate the distal portion 32 of the screw 30), the interior wall 98 also defines a set of slots 62 that extend outwards from the opening 28 in opposite directions. When the trial liner 20 is being pressed onto the distal portion 32 (e.g., head) of the screw 30, the slots 62 allow the opening 28 to at least temporarily enlarge (e.g., the diameter of the opening 28 may increase) to accommodate the screw 30. While two slots 62 have been empirically determined to provide the desired amount of deflection and structural rigidity for the trial liner 20, in other embodiments, the number of slots 62 may differ.

Still referring to FIG. 1, in the illustrative embodiment, the trial liner 20 includes multiple keys or tabs 60 connected to and spaced around an outer circumference of the rim 22. Each key 60 may be embodied as a protrusion of the outer wall 26 that extends radially outward from the rim 22 of the trial liner 20 and is sized and shaped to engage with one of multiple slots 52 (e.g., recesses) defined in the inner wall 44 and rim 42 of the shell 40. When the keys 60 are engaged with (e.g., fitted into) the corresponding slots 52, the keys 60 resist rotation of the trial liner 20 within the shell 40. However, while the opening 28 is shaped to fit securely around the distal portion 32 (e.g., head) of the screw 30 to resist lateral and longitudinal movement of the trial liner 20 relative to the screw 30 (as described in more detail), the screw 30 may rotate independently of the trial liner 20. As such, the screw 30 may be rotated into secure engagement with the threaded recess 50 of the shell 40 without dislodging the keys 60 from the corresponding slots 52.

As shown, in the illustrative embodiment, the trial liner 20 includes four keys 60, spaced approximately 90 degrees from each other around the circumference of the rim 22. While in other embodiments, the number and spacing of keys 60 around the rim 22 may be different, four keys 60 spaced equidistantly around the rim 22 has been empirically determined to provide sufficient resistance to rotation while minimizing the amount of material used to produce the trial liner 20. Additionally, in the illustrative embodiment, the shell 40 has more than four slots 52 located around the rim 42. As will be appreciated by those skilled in the art, increasing the number of available slots 52 defined in the rim 42 may decrease the time and effort spent by a surgeon to align the keys 60 with corresponding slots 52. The slots 52 defined in the rim 42 also allow the surgeon to replicate the position of the trial liner relative to the definitive implant when the trial liner 20 has augmented features that provide additional constraint at the rim (e.g., to properly align augmented the liner with the shell 40 to obtain a desired range of motion).

Figure 2:
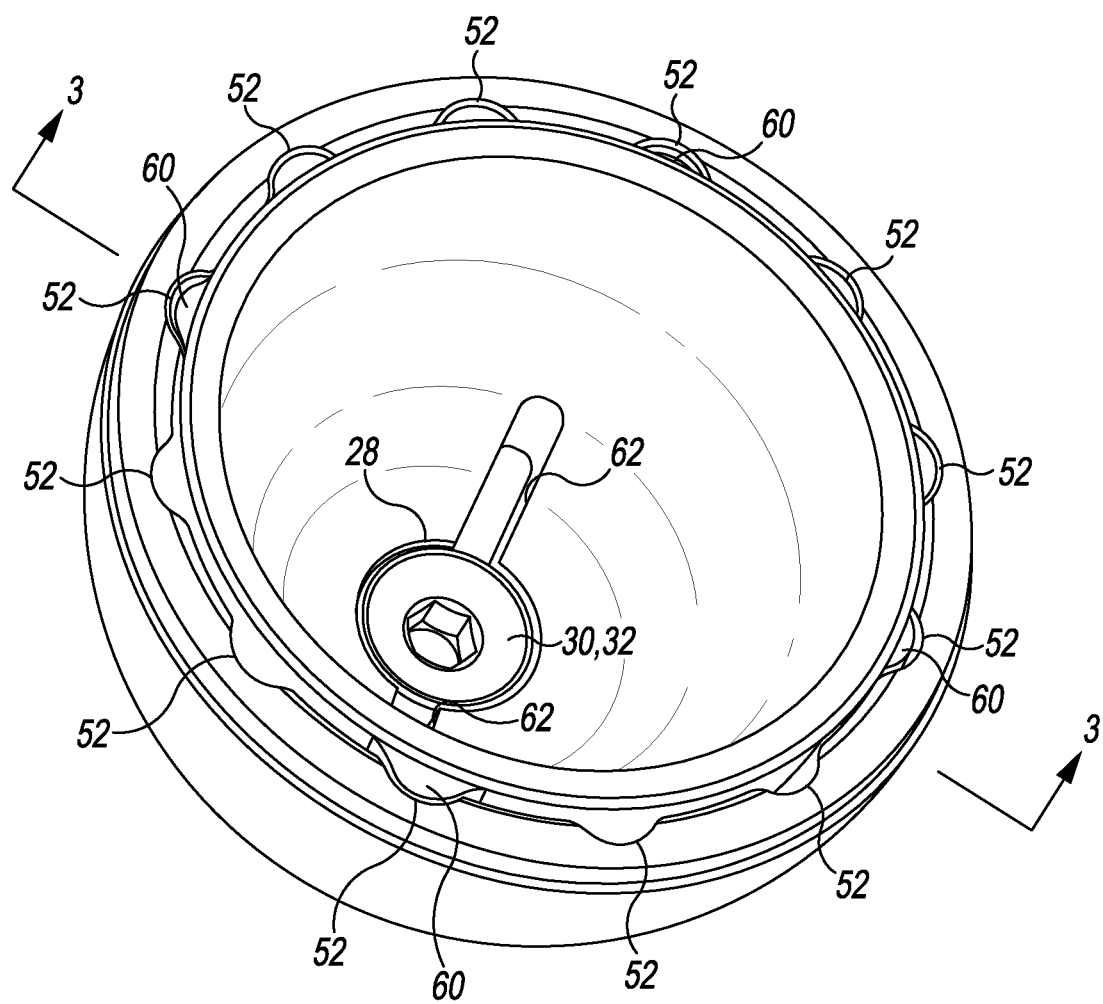
FIG. 2 is a perspective view of the modular acetabular trial liner system of FIG. 1.

As shown more clearly in FIG. 2, in the illustrative embodiment, each key 60 of the trial liner 20 fits within a corresponding one of the slots 52 of the shell 40, to resist clockwise and counterclockwise rotation of the trial liner 20, once engaged. While some embodiments of the trial liner 20 are substantially symmetrical, other embodiments of the trial liner 20 may be asymmetrical, such that unintended rotation of the trial liner 20 within the shell 40 may cause undesired changes in the fit of a femoral head received within the trial liner 20 and/or in the range of motion provided by the system 10. The system 10, as assembled in FIG. 2, may be located within a patient's acetabulum (e.g., during a hip arthroplasty surgical procedure) and, starting from the assembled state, the trial liner 20 may be pulled off of the screw 30, with the body 96 of the trial liner 20 deflecting to allow the distal portion 32 of the screw to withdraw from the opening 28, and another trial liner 20 may be pressed onto the screw 30 (e.g., fitted onto the distal portion 32 of the screw 30, with the body 96 of the replacement trial liner 20 deflecting to accept the screw 30 into the opening 28) without the need to decouple the screw 30 from the shell 40.

Figure 3:
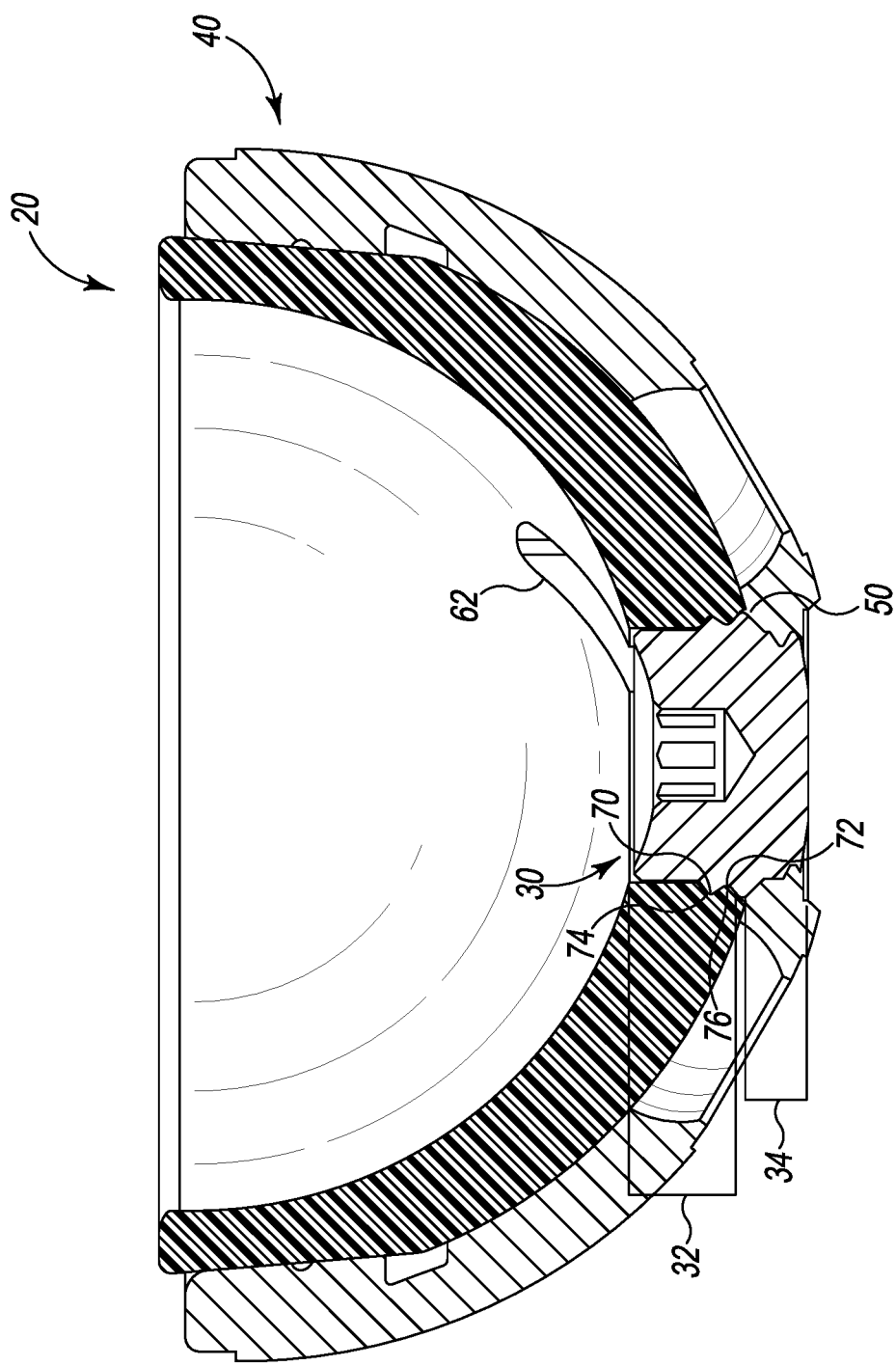
FIG. 3 is a cross-sectional elevation view of the modular acetabular trial liner system of FIG. 1 taken generally along line 3-3 in FIG. 2.

Referring now to FIG. 3, as seen in cross-section along line 3-3 of FIG. 1, the trial liner 20 and the screw 30, in the illustrative embodiment, include physical features shaped to resist lateral and longitudinal movement of the trial liner 20 relative to the screw 30 (and relative to the shell 40, once the screw 30 has been secured into the recess 50). In particular, in the illustrative embodiment, the screw 30 includes a male barb 70 which may be embodied as a protrusion from the circumference of the screw 30, and a female groove 72 which may be embodied as a recess around the circumference of the screw 30. The male barb 70 and female groove 72 of the screw 30 are shaped to engage with (e.g., abut) a corresponding female groove 74 (e.g., a recess) and male barb 76 (e.g., a protrusion) defined in the trial liner 20. In some embodiments, the trial liner 20 may have an undercut distal to the male barb 76 to assist in deflection. When the screw 30 is secured into the shell 40, an proximal portion 34 of the screw 30 engages with the threaded recess 50 of the shell 40.

Figure 4:
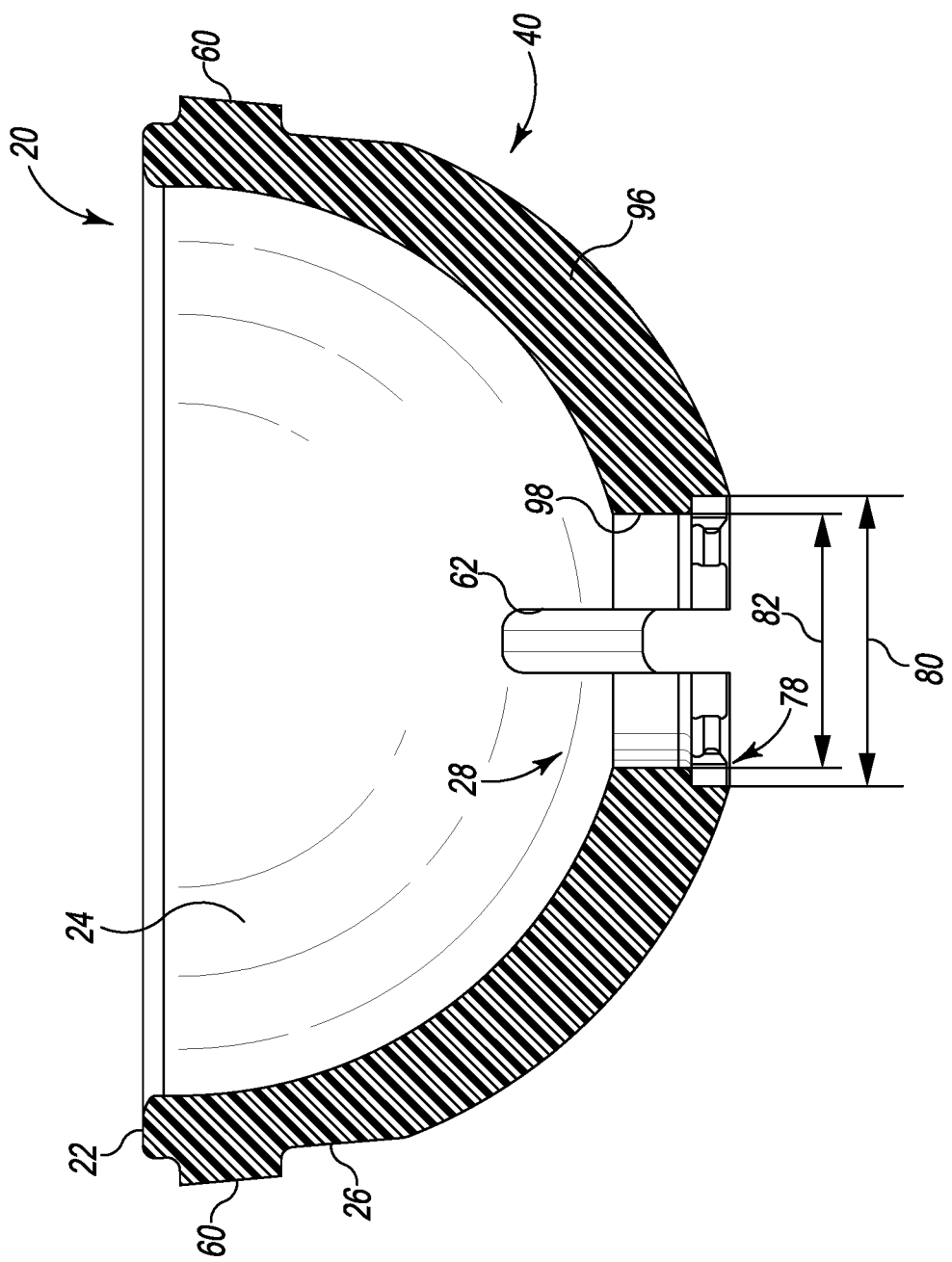
FIG. 4 is a cross-sectional elevation view, similar to FIG. 3, of an embodiment of a trial liner of the modular acetabular trial liner system of FIG. 1.
Figure 5:
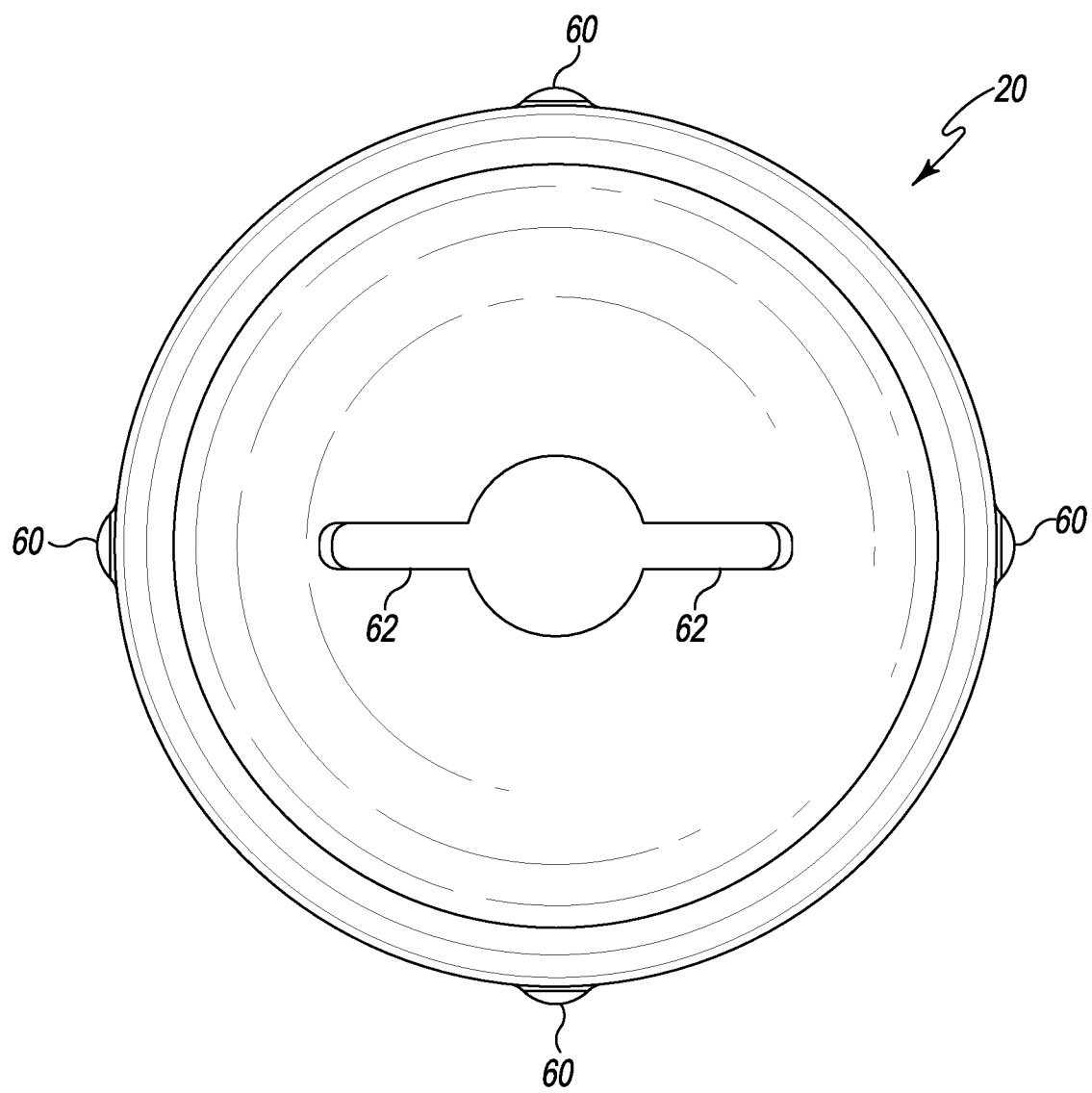
FIG. 5 is a plan view of the trial liner of FIG. 4.

FIG. 4 provides another cross-sectional view of the trial liner 20, slightly rotated from the view provided in FIG. 3, and with the screw 30 and shell 40 removed. As shown, the outer wall 26 is shaped, near the rim 22, to define the keys 60, which extend outwards from the trial liner 20. As mentioned above, and as shown in FIG. 4, the trial liner 20 may include an undercut 78, which may be embodied as a portion of the opening 28 (defined by the interior wall 98) located closer to the outer wall 26 than the inner wall 24 and that has a diameter 80 that is greater than a diameter 82 of a portion of the opening 28 that is closer to the inner wall 24. As such, when the distal portion 32 of the screw 30 is received into the opening 28, the undercut 78 assists in deflection (e.g., bending) of the trial liner 20 material to accommodate the screw 30. Referring briefly to FIG. 5, the slots 62, which extend in opposite directions from the opening 28, assist in deflection of the trial liner 20 material, when the distal portion 32 of the screw 30 is being inserted into or removed from the trial liner 20. Additionally, from a plan view, it can be clearly seen that the keys 60 are spaced approximately equidistantly (e.g., about 90 degrees apart) around the rim 22 of the trial liner 20.

Figure 6:
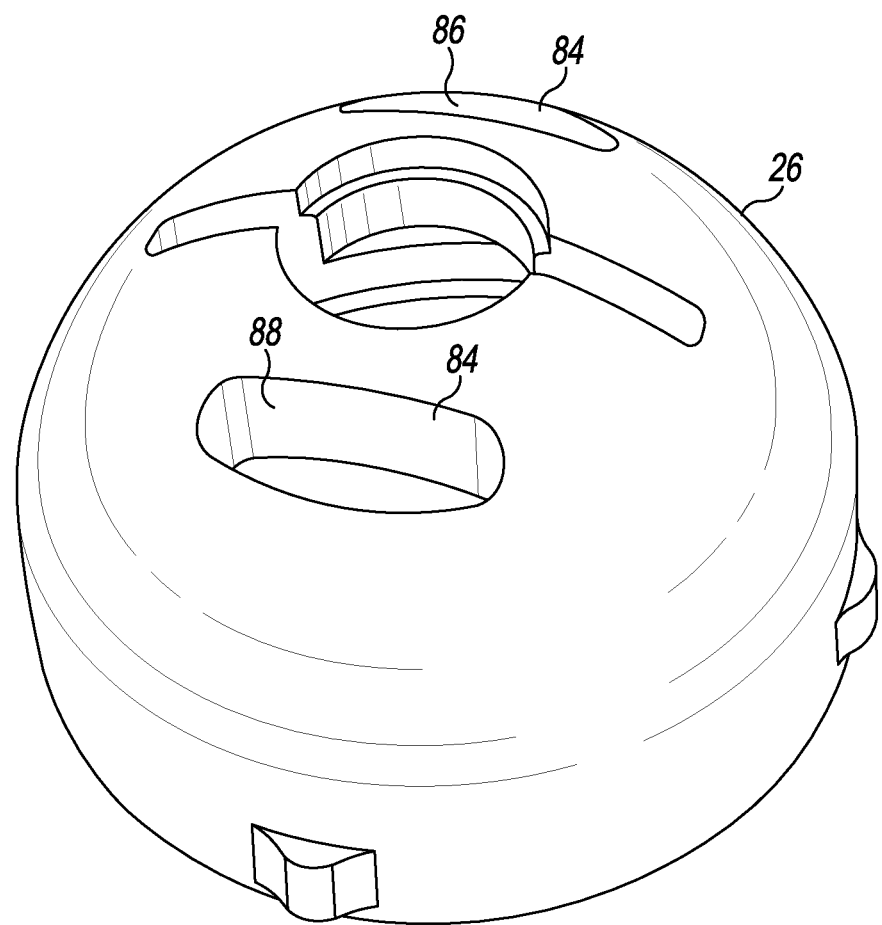
FIG. 6 is bottom perspective view of the trial liner of FIG. 4 showing slots that assist in insertion and removal of the trial liner from a corresponding acetabular shell of the modular acetabular trial liner system of FIG. 1.

Referring now to FIG. 6, in some embodiments, slots 84 may be defined by interior walls 86, 88 that extend between the walls 24, 26 of the trial liner 20. The slots 84, in the illustrative embodiment, are sized and shaped to receive forceps or a similar tool used by a surgeon in the insertion, removal, rotation, deflection and/or other manipulation of the trial liner 20 during the surgical procedure. Additionally, the slots 84 allow the surgeon to see through at least a portion of the trial liner 20 to the shell 40, which may be useful when the surgeon is verifying the alignment of the trial liner 20 within the shell 40 and confirming that the trial liner 20 is properly seated and secured into the shell 40.

Figures 7, 8:
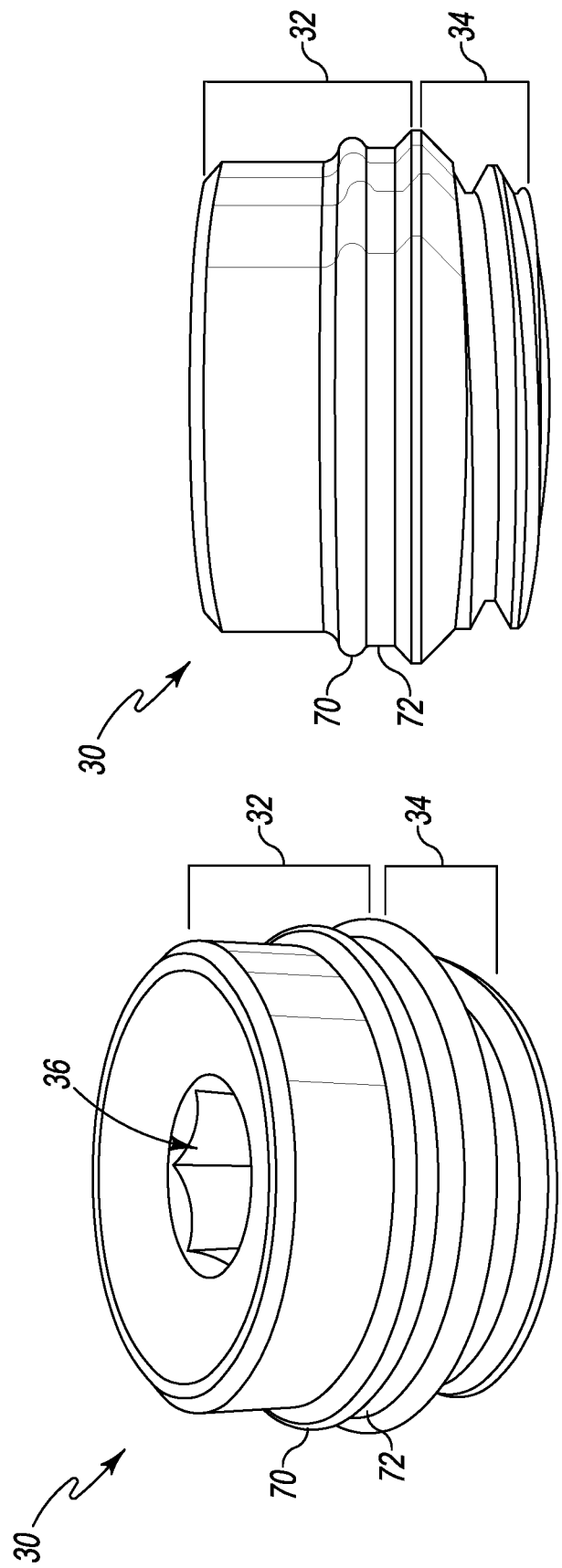
FIG. 7 is a perspective view of an embodiment of a threaded screw shaped to couple the trial liner to the acetabular shell of the modular acetabular trial liner system.
FIG. 8 is an elevation view of the threaded screw of FIG. 7.

Referring briefly to FIGS. 7 and 8, a perspective view and an elevation view of the screw 30 are provided. As described above, the distal portion 32, which includes the male barb 70 and the female groove 72 are received within the trial liner 20. Further, and as stated above with reference to FIG. 3, the proximal portion 34 of the screw 30 engages with the threaded recess 50 of the shell 40. The screw 30 also includes a recess 36 defined in the distal portion 32 to receive a screw driver 94 (shown in FIG. 15) or other tool used by the surgeon to guide the screw 30 towards, and rotate the proximal portion 34 into, the threaded recess 50 of the shell 40. In some embodiments, the first thread of the screw 30 may be removed to create a "blunt start" to provide feedback, to the surgeon, indicative of whether the screw 30 has dropped into the mating screw hole (e.g., the threaded recess 50).

Figure 9:
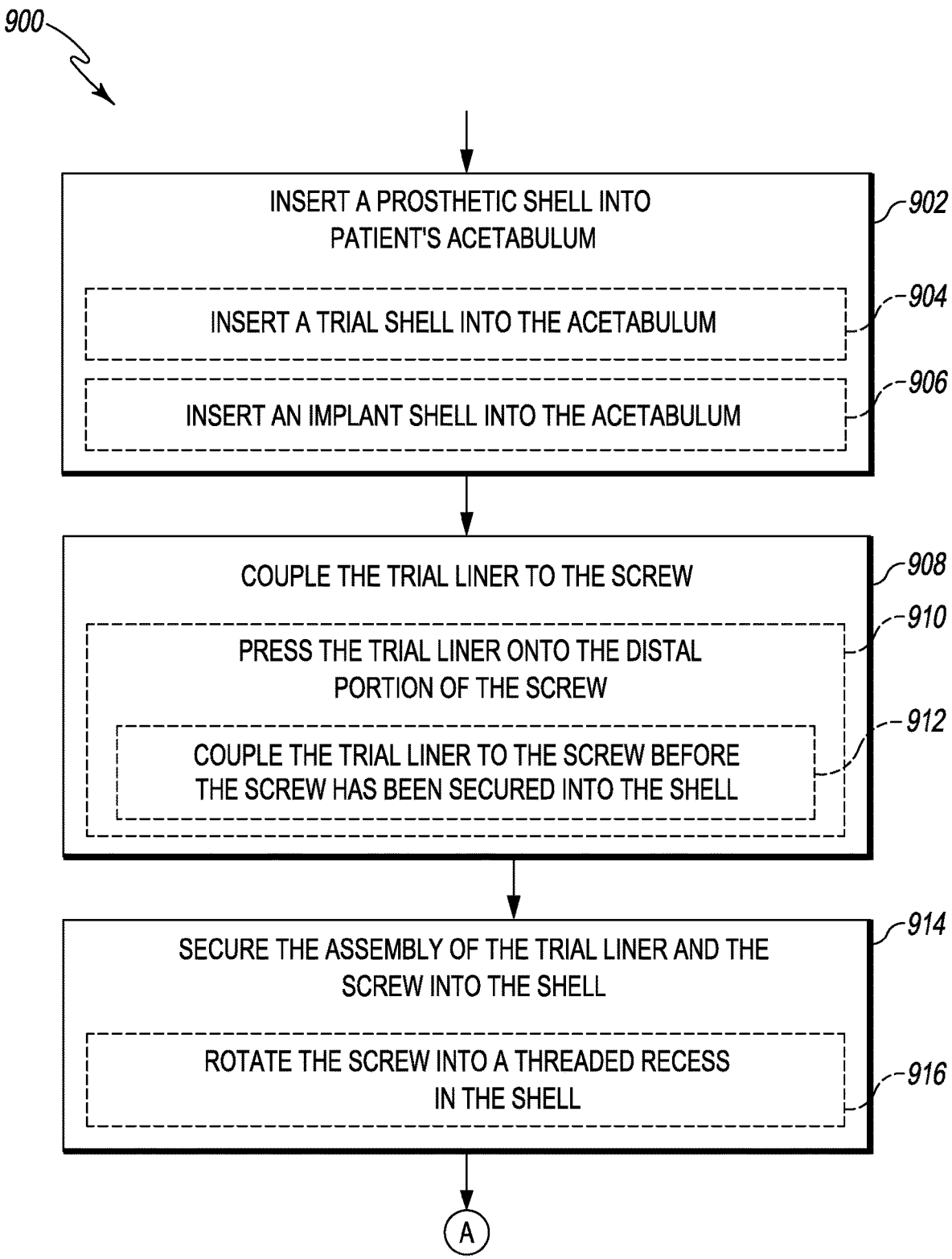
FIGS. 9-11 are a flow chart of at least one embodiment of a method for using the modular acetabular trial liner system of FIG. 1 in a hip arthroplasty surgical procedure.
Figure 12:
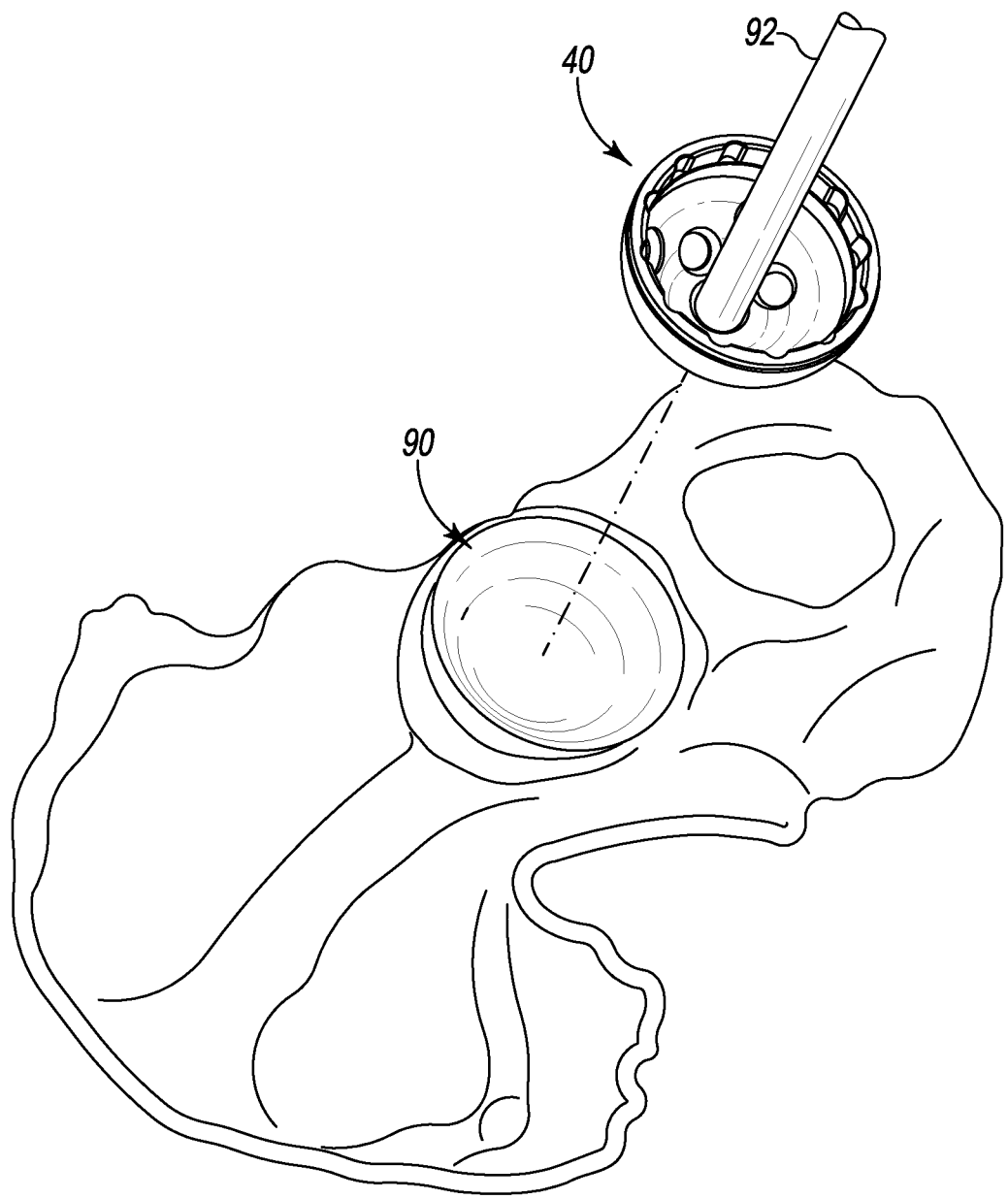
FIG. 12 is a perspective view of a patient's acetabulum with an acetabular shell of the modular trial liner system being advanced towards the acetabulum.
Figure 13:
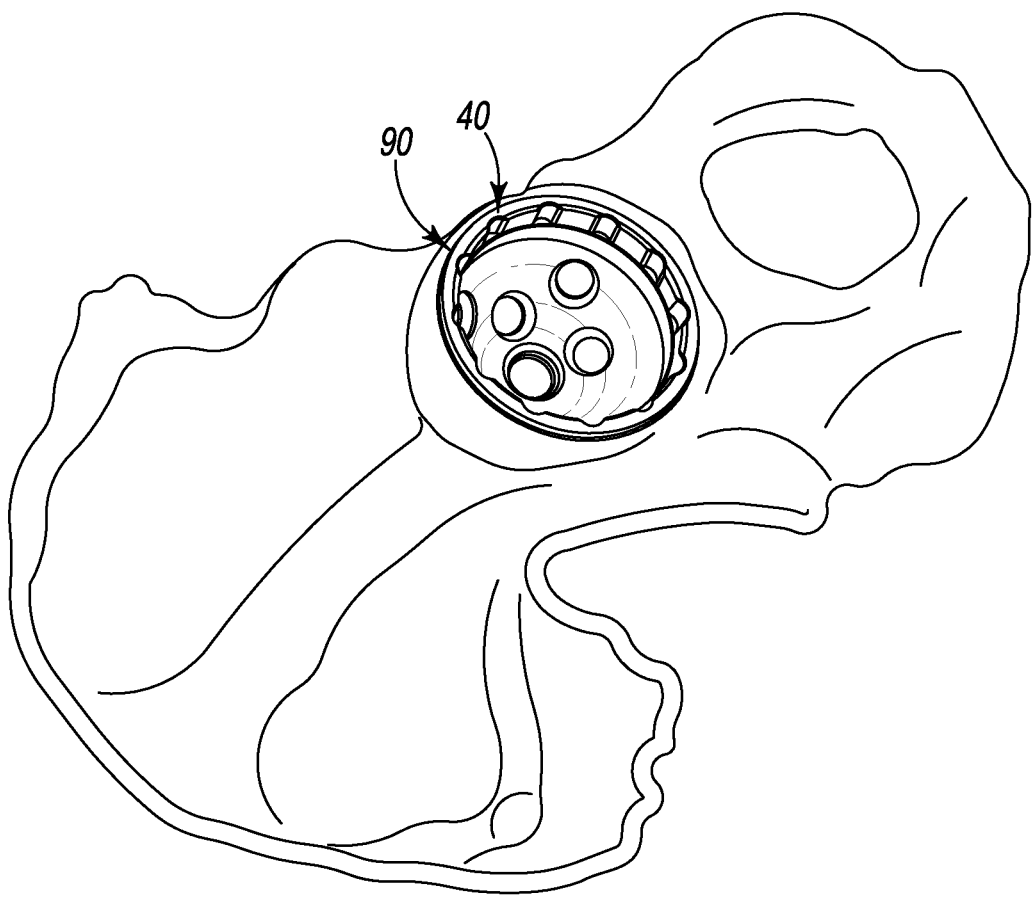
FIG. 13 is a perspective view of the patient's acetabulum with the acetabular shell inserted into the acetabulum.

Referring now to FIG. 9, a surgeon may perform a hip arthroplasty surgical method 900 using the modular acetabular trial liner system 10. Although the method 900 is described as being performed by a surgeon, it should be understood that one or more operations of the method 900 may be performed by another person (e.g., a surgeon's assistant, a second surgeon, etc.). Furthermore, while the steps of the method 900 are shown in a particular order, it should be understood that some of the steps may be performed in a different order or concurrently. In the illustrative embodiment, the method 900 begins in block 902, in which the surgeon inserts (e.g., secures) a prosthetic shell (e.g., the shell 40) into a patient's acetabulum 90, as shown in FIGS. 12 and 13. The acetabulum 90, in the illustrative embodiment, may be surgically prepared (e.g., by a surgical reamer) for insertion of the shell 40. As indicated in block 904, the surgeon may insert a trial shell (e.g., an instrument) into the acetabulum. Alternatively, the surgeon may insert a permanent shell (e.g., an implant) into the acetabulum, as indicated in block 906. The surgeon may press fit the shell 40 into place, using a driver tool 92. In some embodiments, the surgeon may additionally thread one or more screws through bores (e.g., the bores 54) in the shell 40 to further secure the shell 40 in the acetabulum. In yet other embodiments, the surgeon may utilize other techniques, such as use of orthopaedic cement, to insert the shell 40 into the acetabulum.

Figure 14:
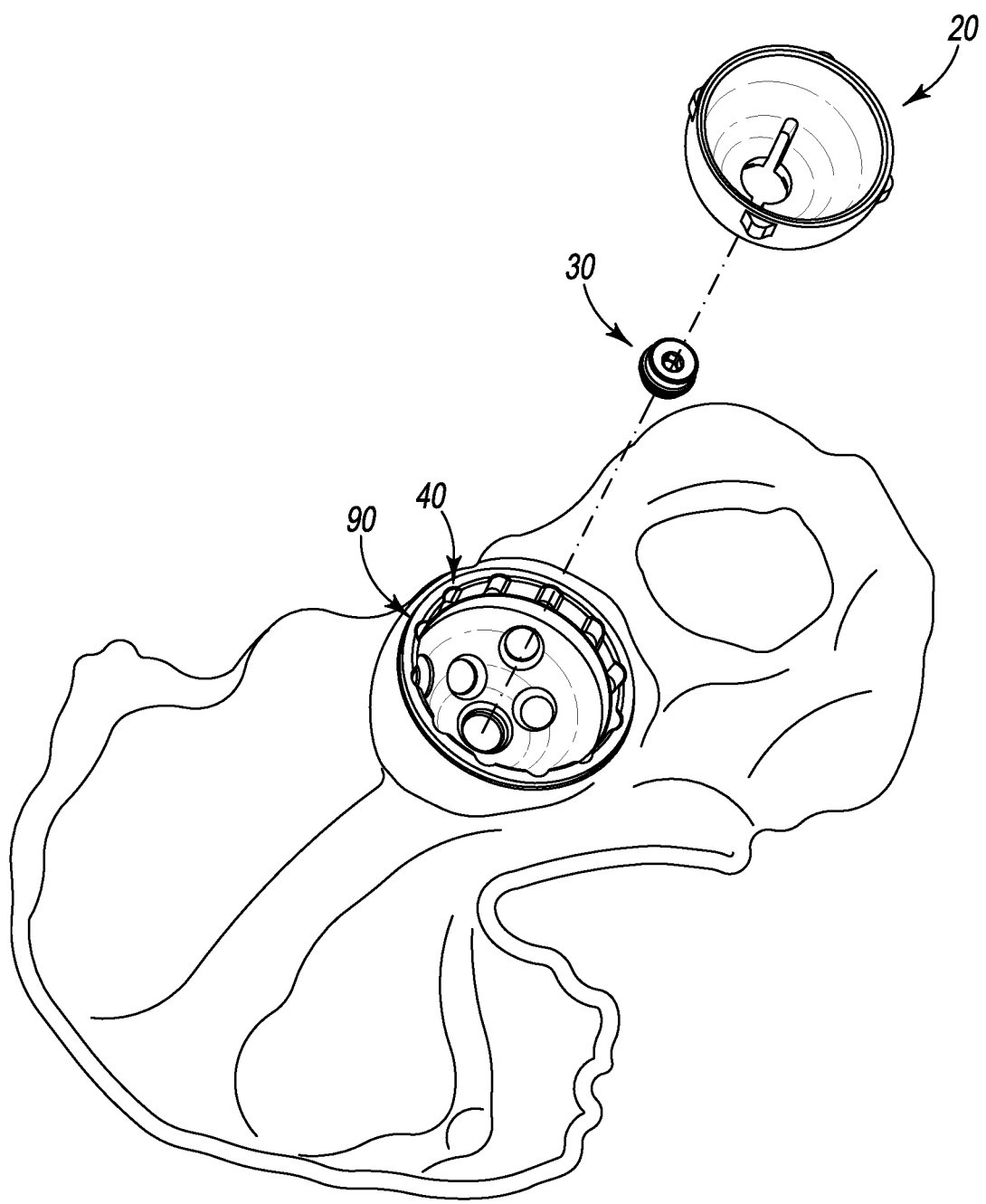
FIG. 14 is a perspective view of the patient's acetabulum with the acetabular shell inserted into the acetabulum and the trial liner in the process of being fitted onto a portion of the screw.

After the shell 40 has been inserted into the acetabulum, the method 900 advances to block 908, in which the surgeon couples the trial liner (e.g., the trial liner 20) to the screw (e.g., the screw 30), as shown in FIG. 14. In coupling the trial liner 20 to the screw 30, the surgeon, in the illustrative embodiment, presses the trial liner 20 onto the distal portion 32 of the screw 30, as indicated in block 910. In doing so, the surgeon, in the illustrative embodiment, couples the trial liner 20 to the screw 30 before the screw has been secured into the shell 40, as indicated in block 912.

Figure 10:
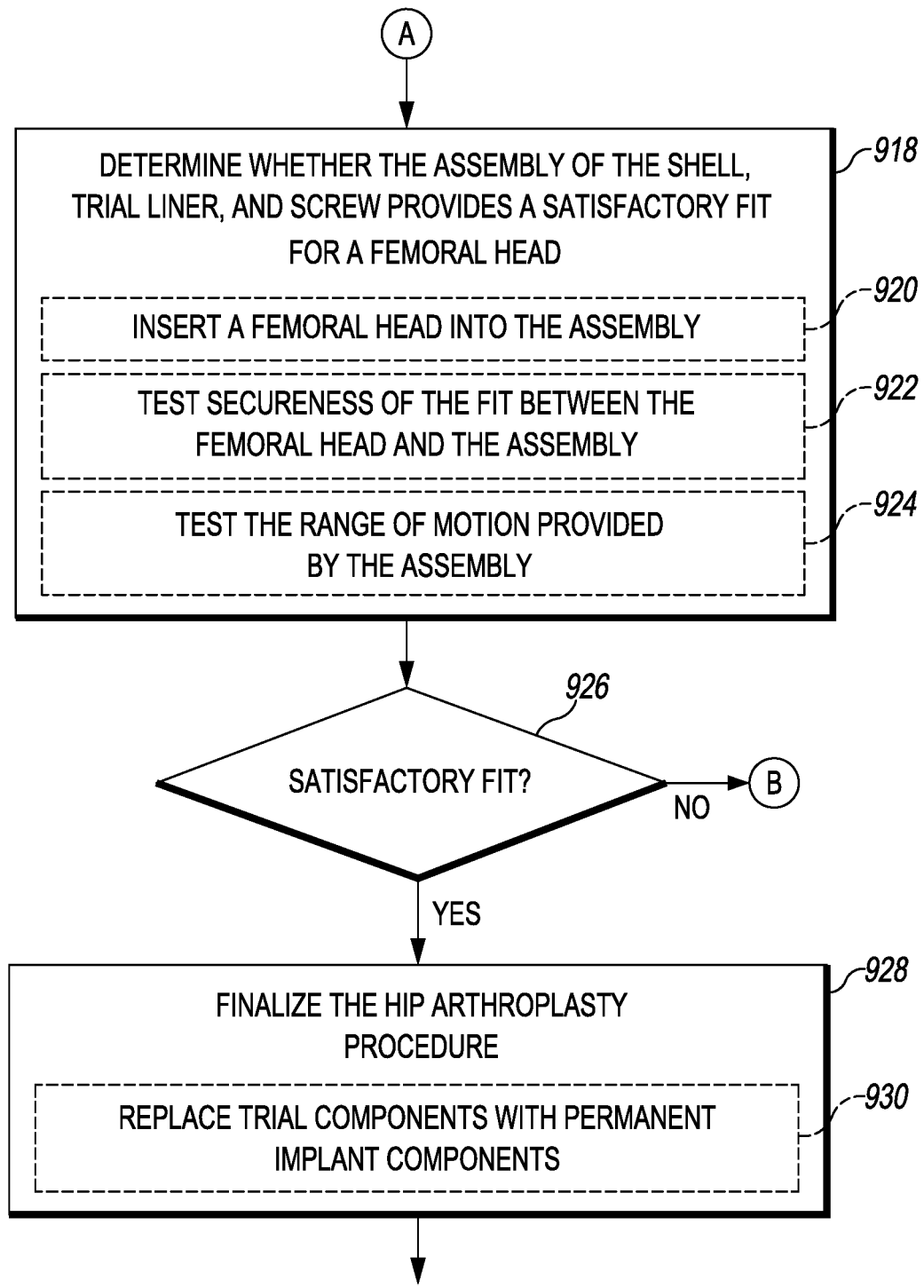
Figure 15:
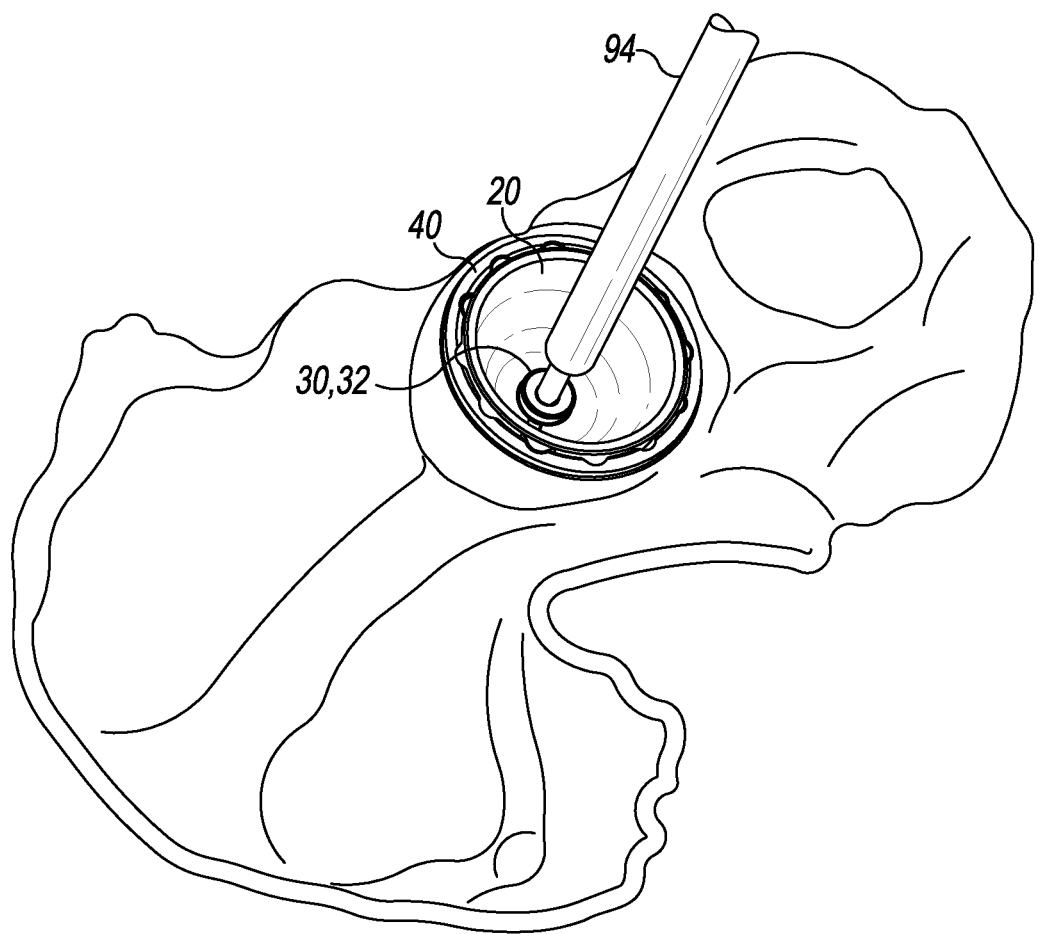
FIG. 15 is a perspective view of the patient's acetabulum with the acetabular shell installed and the screw and trial liner positioned in the shell, and a screw driver tool being used to secure the screw into the shell.
Figure 16:
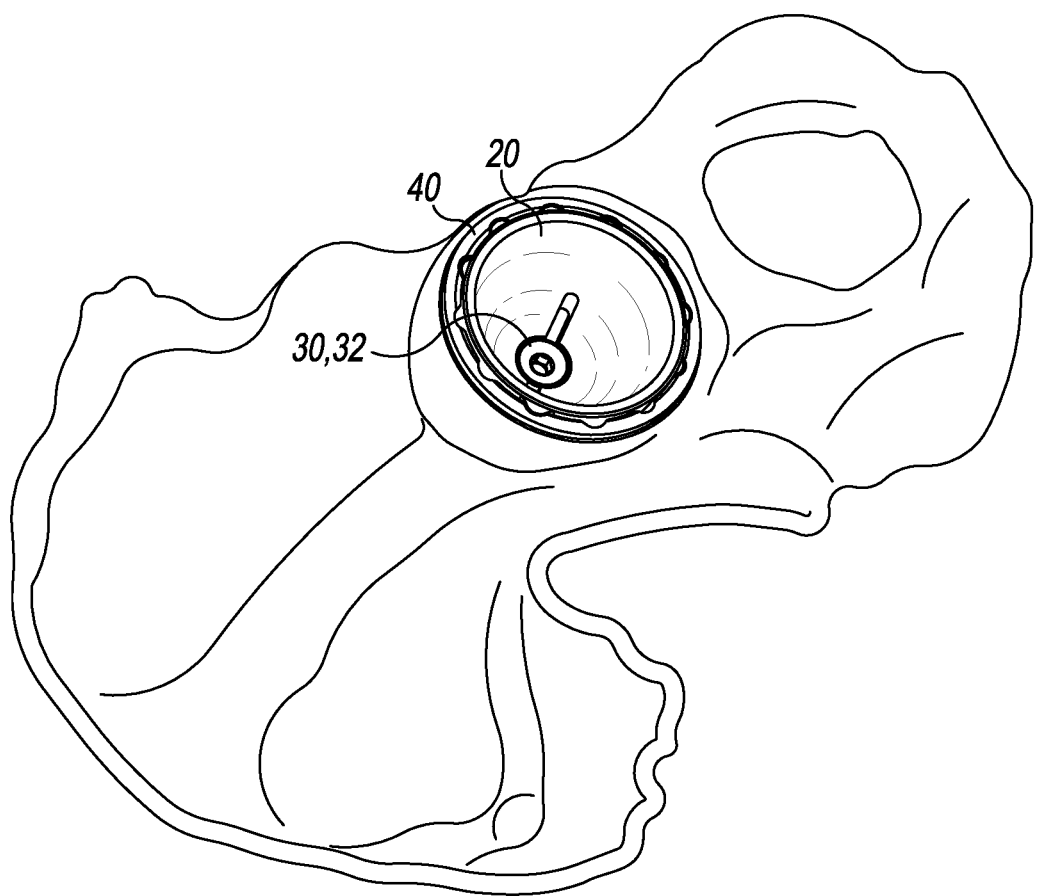
FIG. 16 is a perspective view of the patient's acetabulum with the acetabular shell, screw, and trial liner installed for testing of fit and range of motion.

In block 914, the surgeon secures the assembly of the trial liner 20 and the screw 30 into the shell 40, as shown in FIGS. 15 and 16. In doing so, the surgeon, in the illustrative embodiment, rotates the screw 30 (e.g., using a screw driver 94) into a threaded recess (e.g., the recess 50) in the shell 40 (e.g., at the polar apex), as indicated in block 916. Subsequently, and now referring to block 918 of FIG. 10, the surgeon determines whether the assembly of the shell 40, the trial liner 20, and the screw 30 provides a satisfactory fit for a femoral head. In doing so, and as indicated in block 920, the surgeon inserts a femoral head into the assembly (e.g., into a cavity defined by the inner wall 24 of the trial liner 20). As indicated in block 922, the surgeon may test the secureness of the fit between the femoral head and the assembly (e.g., by testing whether the fit can withstand a target amount of tension without releasing the femoral head from the trial liner 20, testing whether the femoral head is unable to translate freely within the trial liner 20, etc.).

The surgeon, in the illustrative embodiment, also tests the range of motion provided by the assembly (e.g., by determining whether the femoral head is able to rotate through a predefined set of movements), as indicated in block 924. Subsequently, in block 926, the surgeon determines the subsequent course of action based on whether the fit is satisfactory. If the fit is satisfactory, the method 900 advances to block 928, in which the surgeon finalizes the hip arthroplasty procedure. In doing so, the surgeon may replace one or more trial components (e.g., the trial liner, a trial shell, etc.) with permanent implant components (e.g., an implant shell, an implant liner, etc.), as indicated in block 930 and/or perform any other operations to finalize the procedure. Referring back to block 926, if the fit is not satisfactory, the method 900 instead advances to block 932 of FIG. 11, in which the surgeon replaces the trial liner with another trial liner having different properties.

Figure 11:
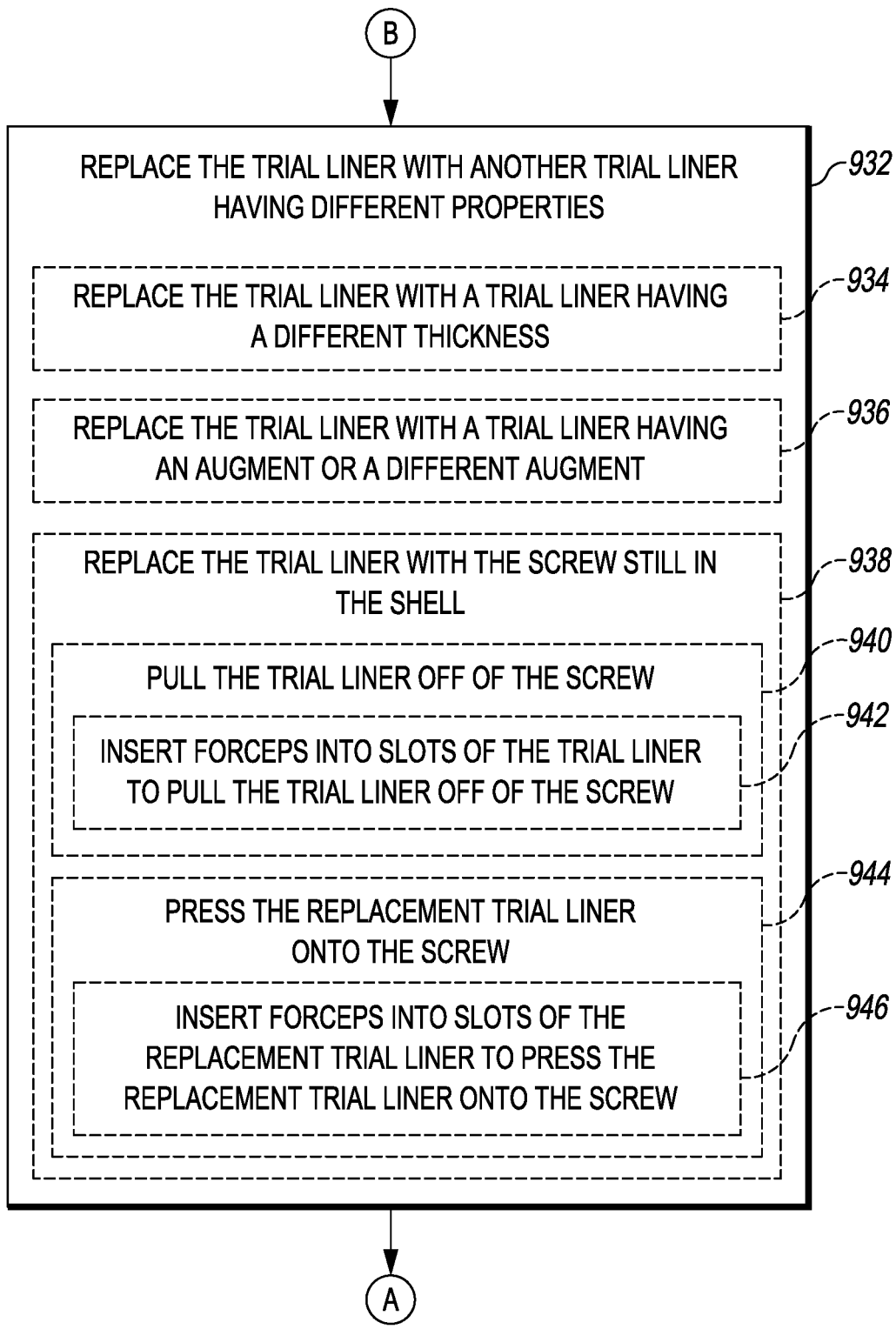

Referring now to FIG. 11, in replacing the trial liner with another trial liner that has different properties, the surgeon may replace the trial liner 20 with a trial liner that has a different thickness (e.g., a thickness between the inner wall 24 and the outer wall 26), as indicated in block 934. Additionally or alternatively, the surgeon may replace the trial liner 20 with a trial liner that has an augment or a different augment than the trial liner 20 being replaced, as indicated in block 936. In other embodiments, the replacement trial liner may have other features (e.g., a trial liner that provides additional constraint in a particular region due to soft tissue laxity, a lateralized trial liner to lateralize the center of the femoral head, etc.). As indicated in block 938, in the illustrative embodiment, the surgeon replaces the trial liner 20 with the screw 30 still in the shell 40 (e.g., still threaded into the threaded recess 50). In doing so, the surgeon pulls the trial liner 20 off of the screw 30 (e.g., causing the body 96 of the trial liner 20 to deflect to allow the screw 30 withdraw from the trial liner 20), as indicated in block 940. In some embodiments, and as indicated in block 942, the surgeon may insert forceps or a similar tool into slots (e.g., the slots 84) of the trial liner 20 to pull the trial liner 20 off of the screw 30.

As indicated in block 944, the surgeon subsequently presses the replacement trial liner onto the screw 30 (e.g., causing the replacement trial liner to deflect to accept the screw into the opening 28). In doing so, the surgeon may insert forceps or a similar tool into slots (e.g., the slots 84) of the replacement trial liner to press the replacement trial liner onto the screw 30. In some embodiments, the trial liner 20 may be designed to seat onto the screw 30 by hand and snap over with an audible snap to indicate that the trial liner 20 is seated. The trial liner 20 may also provide tactile feedback when inserted by hand. Additionally, in some embodiments, the trial liner 20 may be designed such that the soft tissue tension, weight, and force, when the femoral head is inserted into the trial liner 20, would seat the trial liner 20 onto the screw 30. Regardless, after the replacement trial liner 20 is in place, the method 900 loops back to block 918 of FIG. 10, in which the surgeon tests the fit of a femoral head with replacement trial liner 20 in place.

While certain illustrative embodiments have been described in detail in the drawings and the foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A trial liner for use in a hip arthroplasty surgical procedure, comprising:
   a rim;
   a concave inner wall extending inwardly from the rim to define a cavity;
   a convex outer wall extending from the rim opposite the inner wall, wherein the rim, the concave inner wall, and the convex outer wall to define a semi-hemispherical body of the trial liner; and
   an interior wall extending between the inner wall and the outer wall and defining (i) an opening at an apex of the semi-hemispherical body and (ii) a set of slots that extend in opposite directions from the opening,
   wherein the semi-hemispherical body is adapted to deflect and modify the opening, when pressed against a head of a screw, to accept the head of the screw within the opening.

2. The trial liner of claim 1, wherein the trial liner is made of a first material and the screw is made of a second material, and the first material is softer than the second material.

3. The trial liner of claim 2, wherein the first material is a polymeric material.

4. The trial liner of claim 1, wherein the interior wall is shaped to define a female groove to engage with a corresponding male barb of the screw to resist lateral and longitudinal movement of the trial liner relative to the screw.

5. The trial liner of claim 1, wherein the interior wall is shaped to define a male barb to engage with a corresponding female groove of the screw to resist lateral and longitudinal movement of the trial liner relative to the screw.

6. The trial liner of claim 1, further comprising one or more additional interior walls extending between the inner wall and the outer wall and shaped to receive forceps to be used in pressing the trial liner onto the head of the screw or pulling the trial liner off of the screw.

7. The trial liner of claim 1, further comprising a plurality of keys that extend outwardly from the outer wall around a circumference of the trial liner, wherein the keys are shaped to engage with corresponding slots of a trial shell to resist rotation of the trial liner within the trial shell.

8. A modular acetabular trial liner system comprising:
   a screw that includes a head and a threaded proximal portion; and
   a trial liner having
      a semi-hemispherical body that includes (i) a rim; (ii) a concave inner wall extending inwardly from the rim to define a cavity; (iii) a convex outer wall extending from the rim opposite the inner wall; and (iv) an interior wall extending between the inner wall and the outer wall and defining an opening at an apex of the semi-hemispherical body and a set of slots that extend in opposite directions from the opening,
      wherein the semi-hemispherical body is adapted to deflect and modify the opening, when pressed against the head of the screw, to accept the head of the screw within the opening.

9. The modular acetabular trial liner system of claim 8, wherein the threaded proximal portion of the screw is shaped to engage with a threaded recess of a trial shell.

10. The modular acetabular trial liner system of claim 9, further comprising the trial shell.

11. The modular acetabular trial liner system of claim 8, wherein the trial liner is made of a first material and the screw is made of a second material, and the first material is softer than the second material.

12. The modular acetabular trial liner system of claim 11, wherein the first material is a polymeric material and the second material is metal.

13. The modular acetabular trial liner system of claim 8, wherein the opening is shaped to define a female groove to engage with a corresponding male barb of the screw to resist lateral and longitudinal movement of the trial liner relative to the screw.

14. The modular acetabular trial liner system of claim 8, wherein the opening is shaped to define a male barb to engage with a corresponding female groove of the screw to resist lateral and longitudinal movement of the trial liner relative to the screw.

15. The modular acetabular trial liner system of claim 8, wherein the body of the trial liner further includes one or more additional interior walls extending between the inner wall and the outer wall and shaped to receive forceps to be used in pressing the trial liner onto the head of the screw or pulling the trial liner off of the screw.

16. The modular acetabular trial liner system of claim 8, further comprising a plurality of keys that extend outwardly from the outer wall around a circumference of the trial liner, wherein the keys are shaped to engage with corresponding slots of the trial shell to resist rotation of the trial liner within the trial shell.

\* \* \* \* \*